(12) United States Patent
Plahey et al.

(10) Patent No.: US 11,426,502 B2
(45) Date of Patent: Aug. 30, 2022

(54) CLEANING CARTRIDGE FOR A CASSETTE PORT IN A DIALYSIS MACHINE

(71) Applicant: Fresenius Medical Care Holdings, Inc., Waltham, MA (US)

(72) Inventors: Kulwinder Plahey, Martinez, CA (US); Lynn Jensen, Concord, CA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 228 days.

(21) Appl. No.: 16/862,938

(22) Filed: Apr. 30, 2020

(65) Prior Publication Data

US 2021/0338914 A1    Nov. 4, 2021

(51) Int. Cl.
*A61M 1/14* (2006.01)
*A61M 1/28* (2006.01)
*A61M 1/16* (2006.01)

(52) U.S. Cl.
CPC ............ *A61M 1/282* (2014.02); *A61M 1/168* (2013.01); *A61M 2205/12* (2013.01); *A61M 2205/8206* (2013.01); *A61M 2209/10* (2013.01)

(58) Field of Classification Search
CPC .............................. A61M 1/168; A61M 1/282
See application file for complete search history.

(56) References Cited

U.S. PATENT DOCUMENTS

| 5,173,125 A | 12/1992 | Felding | |
|---|---|---|---|
| 2010/0241062 A1* | 9/2010 | Morris | A61M 1/14 604/29 |
| 2014/0027363 A1* | 1/2014 | Heyes | A61M 1/1668 210/175 |

OTHER PUBLICATIONS

3M, "3M™ Double Coated Tape 9443NP", 9443NP Datasheet, Jul. 2006 (Year: 2006).*
International Search Report and Written Opinion for International application No. PCT/US2021/018165, dated Jun. 9, 2021, 11 pages.

* cited by examiner

*Primary Examiner* — Nathan R Price
*Assistant Examiner* — Courtney B Fredrickson
(74) *Attorney, Agent, or Firm* — KDB

(57) ABSTRACT

Dialysis systems and methods for operating dialysis machines (e.g., peritoneal dialysis machines) for conducting dialysis treatments are disclosed. The dialysis system may include a dialysis machine for transferring dialysate to a patient from a dialysate source. The dialysate may flow from the dialysate source through a cassette (e.g., a disposable cassette) positionable within a port formed in the dialysis machine. The dialysis system may also include a cleaning cartridge insertable into the port. The cleaning cartridge may be arranged and configured to collect, remove, etc. any foreign material or debris from the port.

8 Claims, 7 Drawing Sheets

CLEANING CARTRIDGE FOR A CASSETTE PORT IN A DIALYSIS MACHINE

FIELD OF THE DISCLOSURE

The disclosure generally relates to dialysis machines, and more particularly to methods and devices for cleaning a cassette port in a dialysis machine.

BACKGROUND

Dialysis machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated PD machines, also called PD cyclers, are designed to control the entire PD process so that it can be performed at home, usually overnight, without clinical staff in attendance.

A dialysis machine, such as a PD machine or cycler (used interchangeably herein without the intent to limit), may include one or more containers (e.g., bags) containing a fluid (e.g., a dialysate) for patient infusion. In PD machines, for example, tubing as fluid lines are inserted into an abdomen of a patient for flowing fresh dialysate and removing used dialysate, waste, and excess fluid.

In a PD machine, fresh dialysate may travel from the one or more containers, through tubing and into a disposable cartridge or cassette (used interchangeably without intent to limit) that may be inserted into a port located in the PD machine. During use, one or more pumps or actuators positioned within the PD machine interact with the disposable cassette to move fluid from the one or more containers to the patient. During its lifespan, the port may become contaminated. For example, dirt, crumbs, or other foreign debris may become trapped within the port. This problem may be worse when the port is positioned horizontally within the PD machine.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for conducting a dialysis treatment is disclosed. The dialysis system comprises a dialysis machine including a port arranged and configured to receive a disposable cassette used in the dialysis treatment, and a cleaning cartridge insertable into the port formed in the dialysis machine, the cleaning cartridge including one or more features arranged and configured to remove foreign debris from the port.

In one or more embodiments, the cleaning cartridge includes an outer profile substantially similar to an outer profile of the cassette.

In one or more embodiments, the cleaning cartridge includes an outer surface, the outer surface arranged and configured to collect foreign debris located in the port so that upon removing the cleaning cartridge from the port, foreign debris is removed from the port.

In one or more embodiments, the outer surface includes a tacky film arranged and configured to collect the foreign debris.

In one or more embodiments, the outer surface includes coated fibers arranged and configured to collect foreign debris.

In one or more embodiments, the cleaning cartridge includes an electrostatic charge so that, upon positioning the cleaning cartridge within the port, any of the foreign debris located in the port is attracted to the cleaning cartridge.

In one or more embodiments, the cleaning cartridge includes a battery-operated vacuum arranged and configured to produce suction to vacuum any of the foreign debris within the port.

In one or more embodiments, the cleaning cartridge includes a battery-operated nozzle arranged and configured to produce forced air to blow any of the foreign debris out of the port.

In one or more embodiments, the cleaning cartridge includes a battery-operated vacuum and nozzle system, the vacuum and nozzle system arranged and configured to produce forced air to blow any of the foreign debris and to produce suction to vacuum any of the foreign debris.

In one or more embodiments, the port extends horizontally in the dialysis machine from a side surface of the dialysis machine.

In one or more embodiments, the cassette includes one or more valves for interacting with one or more pumps in the dialysis machine for transferring dialysate from the dialysate source to the patient.

According to another exemplary embodiment of the present disclosure, a method for cleaning a cassette port in a dialysis machine is disclosed. The method comprises inserting a cleaning cartridge into a cassette port of a dialysis machine, the dialysis machine for performing a dialysis treatment and including the cassette port arranged and configured to receive a disposable cassette in fluid communication with the patient, and removing the cleaning cartridge and any foreign debris from the cassette port.

In one or more embodiments, the cassette port is horizontally disposed in the dialysis machine.

In one or more embodiments, the cleaning cartridge includes an outer surface arranged and configured to collect foreign debris located in the port so that upon removing the cleaning cartridge from the port, any of the foreign debris is removed from the port.

In one or more embodiments, the outer surface includes a tacky film arranged and configured to collect any of the foreign debris.

In one or more embodiments, the outer surface includes coated fibers arranged and configured to collect foreign debris.

In one or more embodiments, the cleaning cartridge includes an electrostatic charge so that, upon inserting the cleaning cartridge within the port, the cleaning cartridge attracts any of the foreign debris located in the port.

In one or more embodiments, the cleaning cartridge includes a battery-operated vacuum so that, upon inserting the cleaning cartridge within the port, activation of the vacuum collects any of the foreign debris located in the port.

In one or more embodiments, the cleaning cartridge includes a battery-operated nozzle so that, upon inserting the cleaning cartridge within the port, activation of the nozzle pushes any of the foreign debris located in the port out of the dialysis machine.

In one or more embodiments, the cleaning cartridge includes a battery-operated vacuum and nozzle system so that, upon inserting the cleaning cartridge within the port, activation of the vacuum and nozzle system pushes and collects any of the foreign debris located in the port out of the dialysis machine.

According to another exemplary embodiment of the present disclosure, a cleaning cartridge insertable into a port formed in a dialysis machine is disclosed. The cleaning cartridge comprises a body having an outer surface and one or more features arranged and configured to facilitate removing foreign materials or debris from the cassette port.

In one or more embodiments, the outer surface is arranged and configured to collect foreign debris located in the port so that upon removing the cleaning cartridge from the port, foreign debris is removed from the port.

In one or more embodiments, the outer surface includes a tacky film arranged and configured to collect the foreign debris.

In one or more embodiments, the outer surface includes coated fibers arranged and configured to collect foreign debris.

In one or more embodiments, the body includes an electrostatic charge so that, upon positioning the cleaning cartridge within the port, any of the foreign debris located in the port is attracted to the cleaning cartridge.

In one or more embodiments, the cleaning cartridge further comprises a battery-operated vacuum arranged and configured to produce suction to vacuum any of the foreign debris within the port.

In one or more embodiments, the cleaning cartridge further comprises a battery-operated nozzle arranged and configured to produce forced air to blow any of the foreign debris out of the port.

In one or more embodiments, the cleaning cartridge further comprises a battery-operated vacuum and nozzle system arranged and configured to produce forced air to blow any of the foreign debris and suction to vacuum any of the foreign debris within the port.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
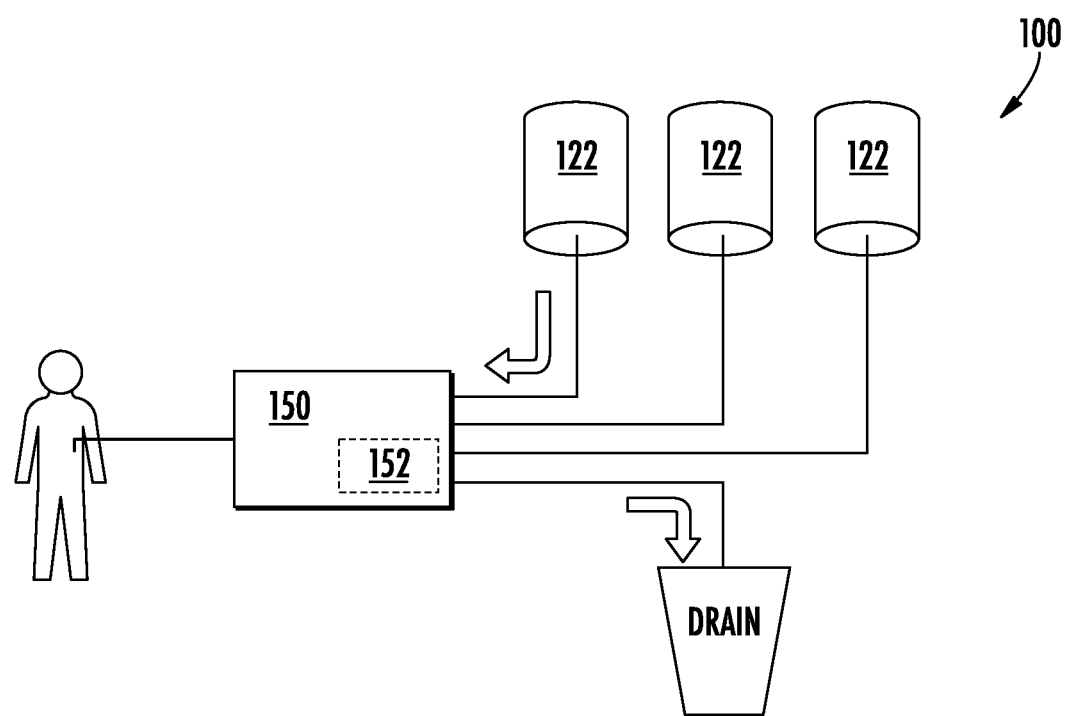
FIG. 1 illustrates an example of an embodiment of a dialysis system.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of a cleaning cartridge will now be described. In use, the cleaning cartridge is arranged and configured to be inserted into a port formed in the PD machine that is configured to receive a cassette (e.g. a disposable cassette) used during a dialysis treatment. The cleaning cartridge is arranged and configured to clean (e.g., remove any foreign debris) the port.

Referring to FIG. 1, a dialysis system 100 may include a PD machine 150, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

One or more dialysate sources may be connected to the dialysis machine 150. In some embodiments, as illustrated, the dialysate source(s) may be dialysate bags 122 that are disposed near the PD machine 150. In an embodiment, the dialysate bags 122 may be hung which may improve air content management as any air content is disposed by gravity to a top portion of the dialysate bag 122. Additionally, and/or alternatively, the dialysate bags 122 may be disposed on shelves below or near the PD machine 150. Valves may be attached to a bottom portion of the dialysate bags 122 so fluid is drawn out and air content delivery is minimized. In one embodiment, as shown, dialysate from the dialysate bags 122 may be transferred to the patient through a warming pouch, a heating chamber, or the like 152 (used interchangeably without the intent to limit) formed in the dialysis machine 150. When the dialysate has reached a predetermined temperature (e.g., approximately 98°-100° F., 37° C.) in the heating chamber 152, the dialysate may be flowed into the patient.

As will be described and illustrated in greater detail below, the dialysate bags 122 may be connected to a cassette, which may be insertable into the dialysis machine 150. In use, the cassette may be connected to dialysate bag lines, which may be used to pass dialysate from dialysate bags 122 to the cassette. In use, the cassette may be disposable. Alternatively, the cassette may be reusable. In addition, a patient line and a drain line may be connected or associated with the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use. Although the system described herein is discussed principally in connection with the use of dialysate bags as the dialysate source, it is noted that, in other embodiments, different dialysate sources may be used. For example, in other embodiments, the dialysate source may include one or more containers in which dialysate is mixed and/or otherwise prepared at the PD cycler from a dialysate concentrate, see, e.g., U.S. Pat. No. 10,076,599 to Eyrard et al., entitled "Dry Peritoneal Dialysis Concentrate System," which is incorporated by reference herein in its entirety.

Figure 2:
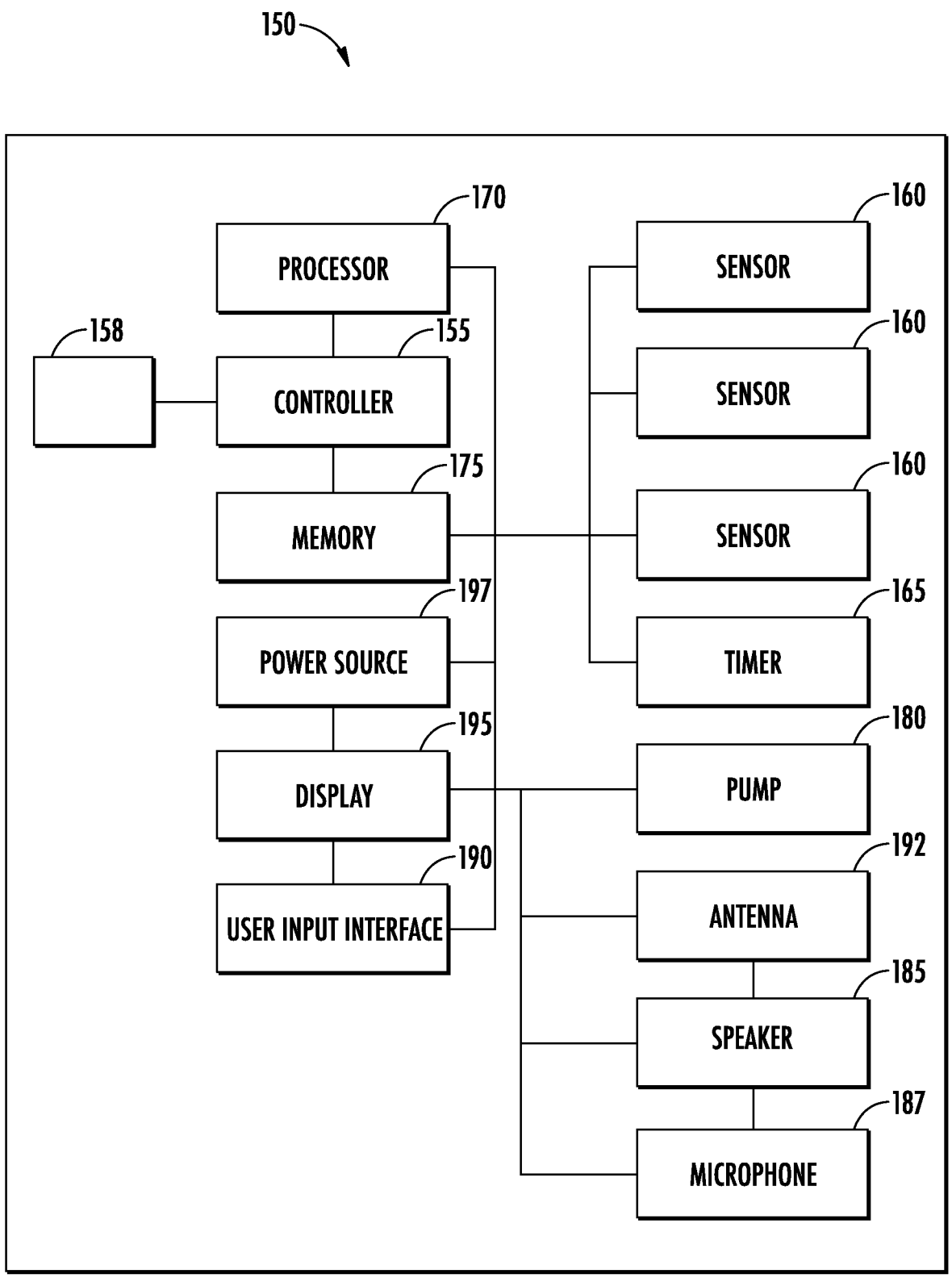
FIG. 2 is a block diagram illustrating an example of an embodiment of a dialysis machine and a controller.

Referring to FIG. 2, a schematic of an exemplary embodiment of a dialysis machine such as, for example, dialysis machine 150 and a controller 155 in accordance with the present disclosure are shown. The machine 150 may be a home dialysis machine, e.g., a PD machine, for performing a dialysis treatment on a patient, and may be included in the system 100 described above with respect to FIG. 1. The controller 155 may automatically control execution of a treatment function during a course of dialysis treatment. The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing triggering of the sensors 160.

In some embodiments, the machine 150 may also include a processor 170, and memory 175, the controller 155, the processor 170, and/or the memory 175, or combinations thereof of the machine 150, may receive signals from the sensor(s) 160 indicating various parameters. Each fluid bag (e.g., the dialysate bags 122) may contain an approximate amount of dialysate, such that "approximate amount" may be defined as a 3L fluid bag containing 3000 to 3150 mL, a 5L fluid bag containing 5000 to 5250 mL, and a 6L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, the dialysis machine 150 may include at least one pump 180 operatively connected to the controller 155. During a treatment operation, the controller 155 may control the pump 180 for pumping fluid, e.g., fresh and spent dialysate, to and from a patient. For example, the pump 180 may transfer dialysate from the dialysate bag 122 through, for example, a cassette insertable into a port formed in the dialysis machine, to the heating chamber 152 prior to transferring the dialysis to the patient. In an embodiment, the pump 180 may be a peristaltic pump. The controller 155 may also be operatively connected to a speaker 185 and a microphone 187 disposed in the machine 150. A user input interface 190 may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The machine 150 may also be wirelessly connectable via an antenna 192 for remote communication. The machine 150 may also include a display 195 and a power source 197.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 150 or may be coupled to the machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3:
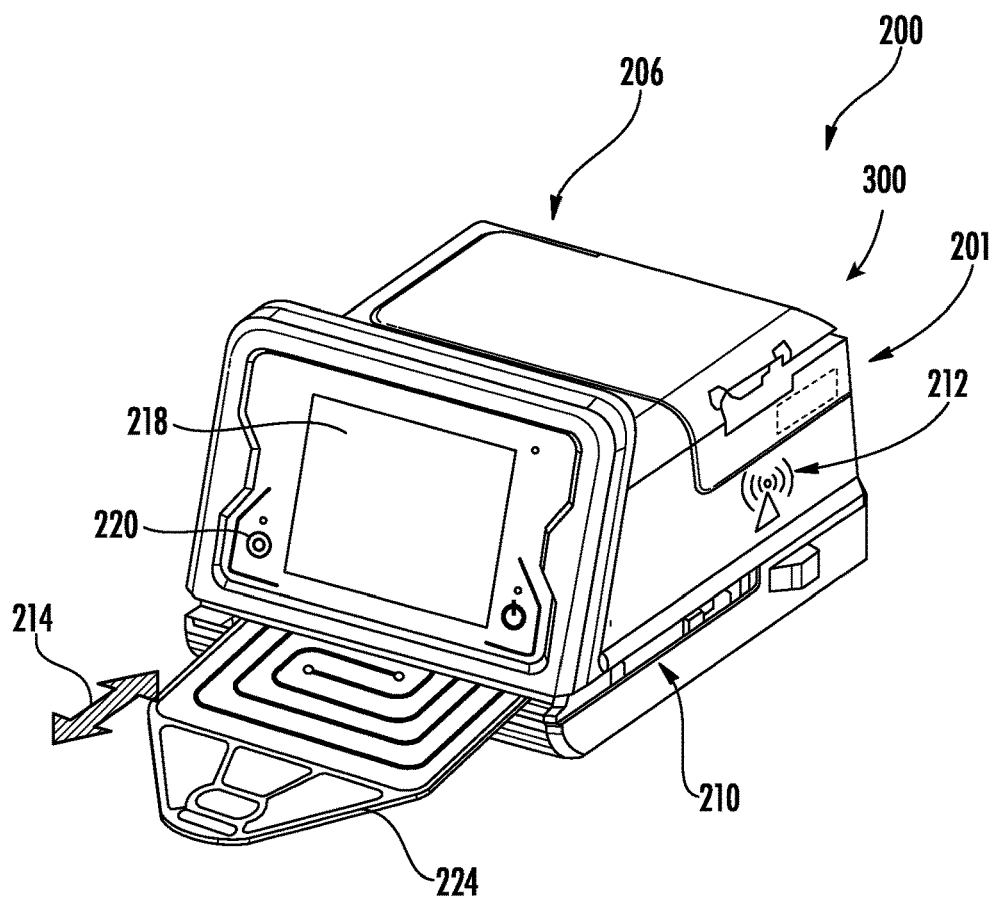
FIG. 3 illustrates a perspective view of an example of an embodiment of a dialysis machine that can be used in the dialysis system of FIG. 1.

FIG. 3 illustrates an example of an embodiment of a dialysis machine 200 such as, for example, dialysis machine 150, that can be used in connection with the dialysis system 100 shown in FIG. 1. The dialysis machine 200 may be implemented in the dialysis system 100 and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment.

The touch screen 218 and the control panel 220 may allow a user to input various treatment parameters to the dialysis machine 200 and to otherwise control the dialysis machine 200. In addition, the touch screen 218 may serve as a display. The touch screen 218 may function to provide information to the patient and the operator of the dialysis system 100. For example, the touch screen 218 may display information related to a dialysis treatment to be applied to the patient, including information related to a prescription.

The dialysis machine 200 may include a processing module 201 that resides inside the dialysis machine 200, the processing module 201 being configured to communicate with the touch screen 218 and the control panel 220. The processing module 201 may be configured to receive data from the touch screen 218, the control panel 220, and sensors, e.g., air, temperature and pressure sensors, and control the dialysis machine 200 based on the received data. For example, the processing module 201 may adjust the operating parameters of the dialysis machine 200. In some embodiments, the processing module 201 may be an MPC823 PowerPC device manufactured by Motorola, Inc.

The dialysis machine 200 may be configured to connect to a network. The connection to network may be via a wired and/or wireless connection. The dialysis machine 200 may include a connection component 212 configured to facilitate the connection to the network. The connection component 212 may be a transceiver for wireless connections and/or other signal processor for processing signals transmitted and received over a wired connection. Other medical devices (e.g., other dialysis machines) or components may be configured to connect to the network and communicate with the dialysis machine 200.

Figure 4:
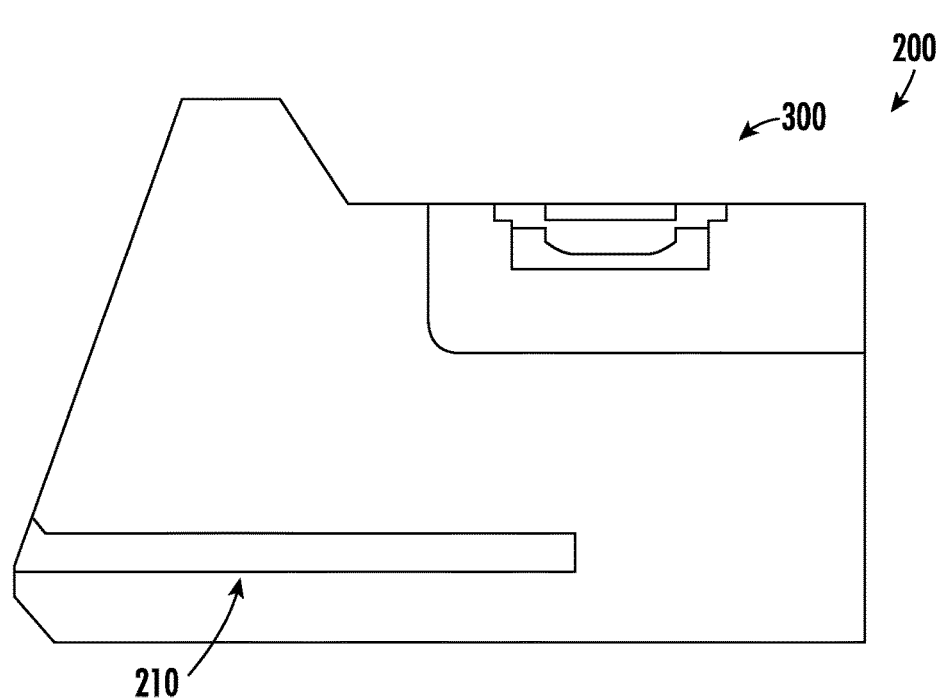
FIG. 4 illustrates a cross-sectional view of the dialysis machine shown in FIG. 3.
Figure 5A:
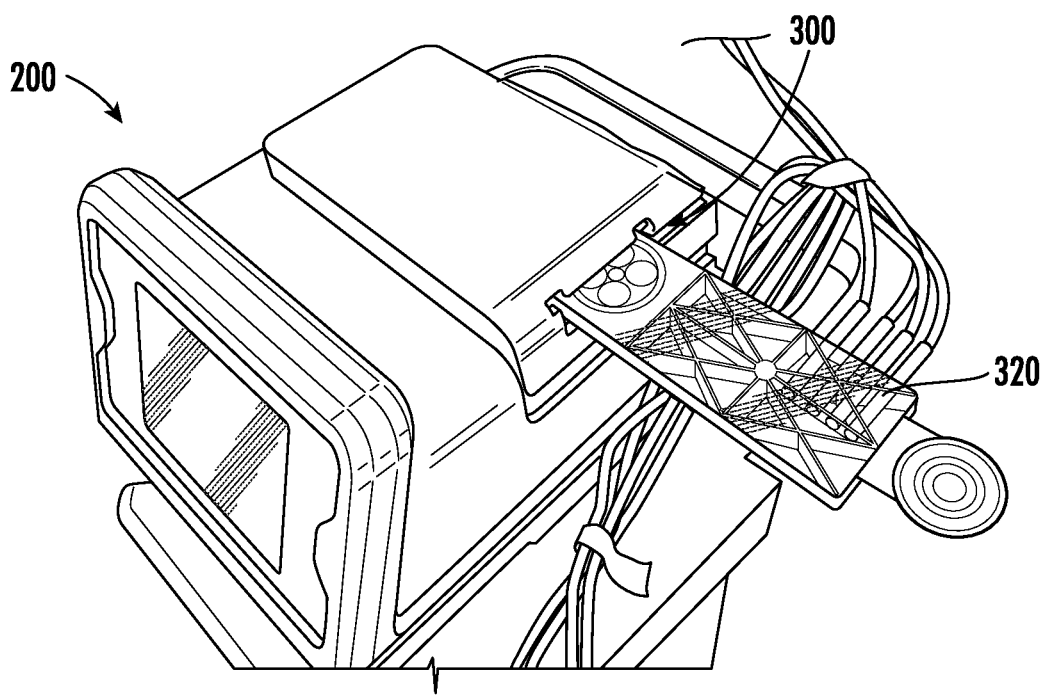
FIGS. 5A and 5B illustrate perspective views of an example of an embodiment of a cassette being inserted into a port formed in the dialysis machine of FIG. 3.
Figure 5B:
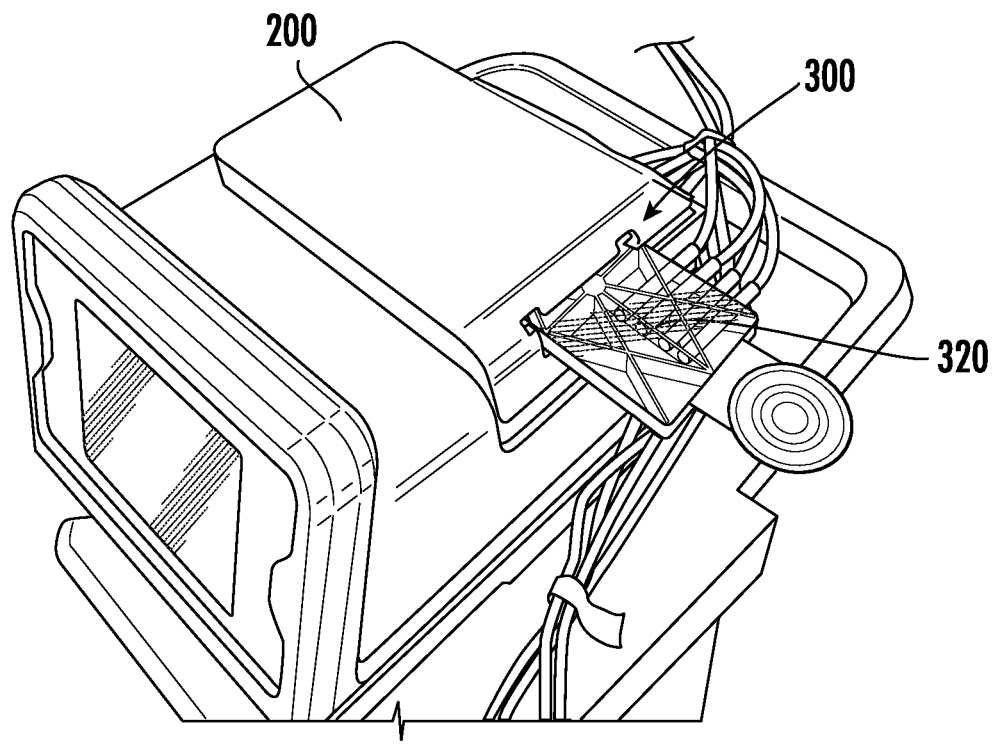
Figure 6:
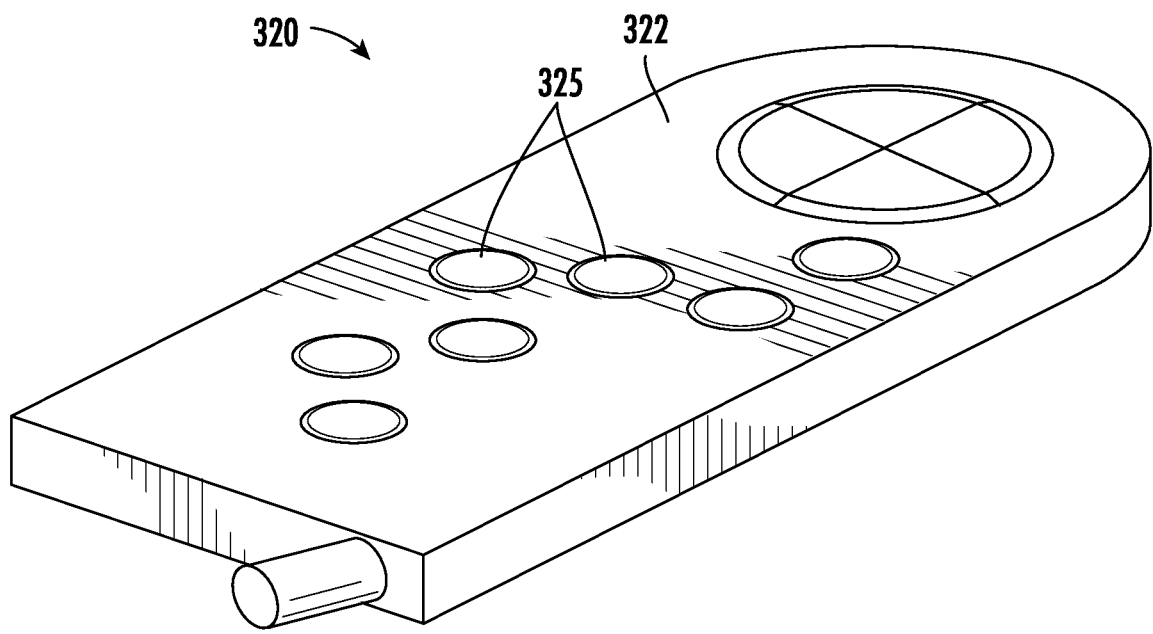
FIG. 6 illustrates a perspective view of an example of an embodiment of the cassette of FIGS. 5A and 5B.

Referring to FIGS. 3 and 4, the PD machine 200 includes a cassette port 300 that is arranged and configured to receive a cassette 320 (FIG. 6) (e.g., as illustrated in FIGS. 5A and 5B, the cassette 320 may be insertable into the cassette port 300 formed in the PD machine 200). As illustrated in FIGS. 3-5B, in one embodiment, the cassette port 300 is arranged horizontally in the PD machine 200 (e.g., extending across the PD machine 200 between side surfaces). In one embodiment, the cassette port 300 may extend from a side surface of the PD machine 200. In use, the cassette 320 may be connected to dialysate bag lines, which may be used to pass dialysate from dialysate bags 122 to the cassette 320. In use, the cassette 320 may be disposable. Alternatively, the cassette 320 may be reusable. Thus arranged, with the cassette 320 positioned in the cassette port 300, the at least one pump 180 positioned within the PD machine 200 may be operated to pump fluid, e.g., fresh and spent dialysate, to and from the patient.

In addition, the dialysis may need to be heated to body temperature prior to being inserted into the patient (e.g., it is preferred that dialysate should be delivered to patients at specific temperatures, for example, at 37 degrees Celsius (e.g., body temperature)). As illustrated in FIG. 3, the PD machine 200 may also include one or more heating elements disposed internal to the machine 200 and an opening or cavity 210 (used interchangeably herein without the intent to limit) arranged and configured to receive a heating cassette 224 in a direction indicated at arrow 214. In use, the heating cassette 224 may be inserted into the opening 210 formed in the PD machine 200 and into the heating chamber 152 positioned with the dialysis machine 200. In some embodiments, the heating cassette 224 may be configured so dialysate may continually flow through the heating cassette 224 to achieve a predetermined temperature before flowing into the patient. For example, in some embodiments the dialysate may continually flow through the heating cassette 224 at a rate of approximately 200 mL/min. Thus arranged, the pump 180 may pump dialysate from the dialysate bag 122 through, for example, the cassette 320 positioned in the cassette port 300, through the heating cassette 224 positioned in the heating chamber 152, and eventually to the patient.

In use, with the heating cassette 224 inserted into the cavity 210, the one or more heating elements may affect the temperature of dialysate flowing through the heating cassette 224. In some embodiments, the heating chamber 152 may be arranged and configured so that a portion of tubing in the system is passed by, around, or otherwise configured with respect to, one or more heating elements. In some embodiments, a dialysis machine 200 may provide an active measurement of the dialysate temperature in dialysate bags and/or a heating chamber, e.g., in the dialysate bags 122, and the heating chamber of FIGS. 1 and 3. It is understood that FIGS. 1 and 3 illustrate dialysate continuously flowing through the heating cassette 224 "in-line" with the dialysis machine 200, reaching an acceptable temperature by the application of internal heating elements.

Referring to FIGS. 3-5B, PD machines 200 utilizing a horizontally positioned cassette port 300 for receiving a disposable cassette 320 is more susceptible to trapping foreign material such as, for example, dirt, crumbs, or other foreign debris. As a result, instances of foreign materials getting trapped within, for example, ridges or grooves situated around valves 325 in a surface 322 of the cassette 320 have occurred. That is, in use with the cassette 320 properly positioned within the cassette port 300, the cassette 320 includes a plurality of valves 325 arranged and configured to interface with one or more actuators or pumps positioned within the PD machine 200. In use, the PD machine 200 may utilize a vacuum to improve contact between the valves 325 formed in the cassette 320 and the actuators or pumps positioned in the PD machine 200. The inclusion of foreign materials or debris within the cassette port 300 at the interface between the valves 325 in the cassette 320 and the actuators or pumps can prevent, or at least inhibit, the formation of a proper seal, which may result in leakage at the interface that degrades the performance of the PD machine 200 or prevents the PD machine 200 from working at all.

Figure 7:
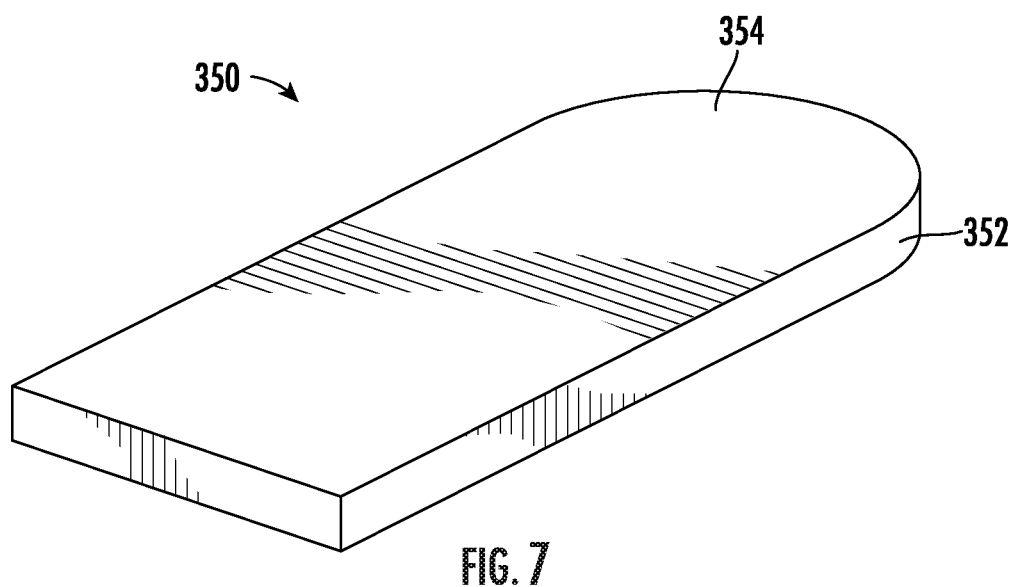
FIG. 7 illustrates a perspective view of an example of an embodiment of a cleaning cartridge that may be used in connection with the dialysis machine of FIG. 3.

In use, access to the interior of the cassette port 300 is rendered difficult. Thus, removing any foreign debris that may become trapped within the cassette port 300 is difficult. In accordance with one or more aspects of the present disclosure, an example embodiment of a cleaning cartridge 350 is shown in FIG. 7. In use, as will be described in greater detail herein, the cleaning cartridge 350 is arranged and configured to be inserted into the cassette port 300 formed in the PD machine 200. The cleaning cartridge 350 may be arranged and configured to clean the cassette port 300 of any foreign debris upon insertion therein. As illustrated, the cleaning cartridge 350 preferably includes an outer profile 352 that is substantially similar to the cassette 320 (e.g., the cleaning cartridge 350 has a body having a physical envelope that substantially matches the shape of the cassette 320 used to pump dialysis through the PD machine 200) so that the cleaning cartridge 350 is arranged and configured to be insertable into the cassette port 300. In use, the cleaning cartridge 350 includes one or more features arranged and configured to facilitate removing foreign materials or debris from the cassette port 300. For example, in one embodiment, the cleaning cartridge 350 includes an outer surface 354 arranged and configured to collect and trap foreign debris. For example, the outer surface 354 may include or be formed from a tacky film that when properly positioned within the cassette port 300, will collect and trap foreign debris that gets struck to the tacky film. Alternatively, for example, the outer surface 354 may include or be formed from coated fibers that when properly positioned within the cassette port 300, will collect and trap foreign debris that gets trapped within the fibers. In either implementation, upon removing the cleaning cartridge 350 from the cassette port 300 foreign material and debris will be removed from the cassette port 300. In one embodiment, the cleaning cartridge 350 may be manufactured from a rigid plastic such as, for example, a polycarbonate, an acrylic, an ABS, a polypropylene, etc.

Figure 8:
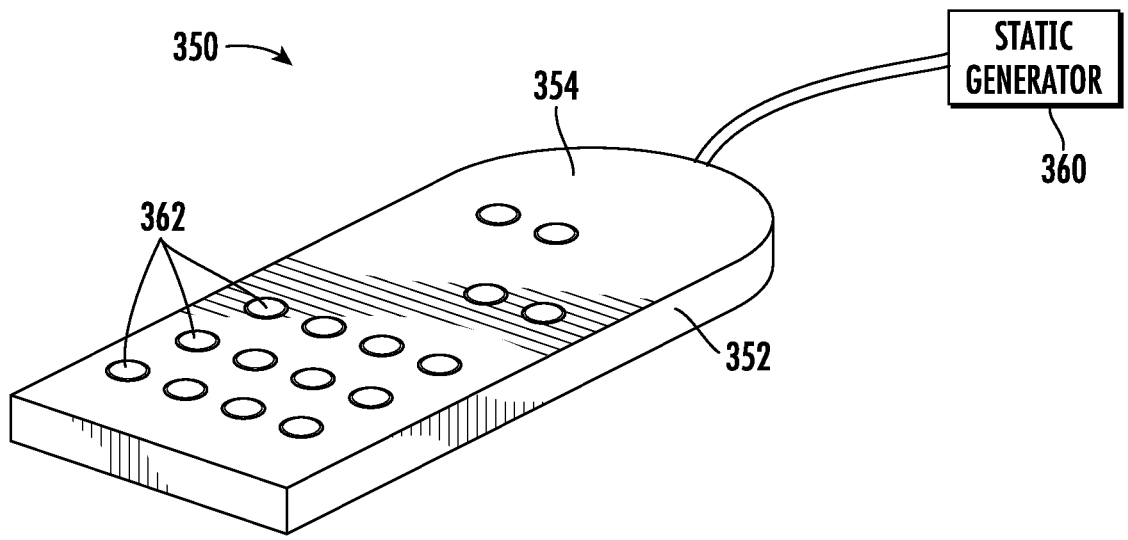
FIG. 8 illustrates a perspective view of another example of an embodiment of a cleaning cartridge that may be used in connection with the dialysis machine of FIG. 3.

In addition, and/or alternatively, referring to FIG. 8, the cleaning cartridge 350 may be arranged and configured to incorporate an electrostatic charge so that, upon positioning the cleaning cartridge 350 within the cassette port 300, any foreign material or debris located in the cassette port 300, will be attracted to the cleaning cartridge 350 and thus removed upon withdrawing the cleaning cartridge 350 from the cassette port 300. For example, as illustrated, the cleaning cartridge 350 may be coupled to a static generator 360. In use, with the cleaning cartridge 350 positioned within the cassette port 300, the static generator 360 generates positive electrostatic charges 362 on the outer surface 354 of the cleaning cartridge 350 to attract and subsequently remove any foreign debris with the removal of the cleaning cartridge 350 from the cassette port 300.

Figure 9:
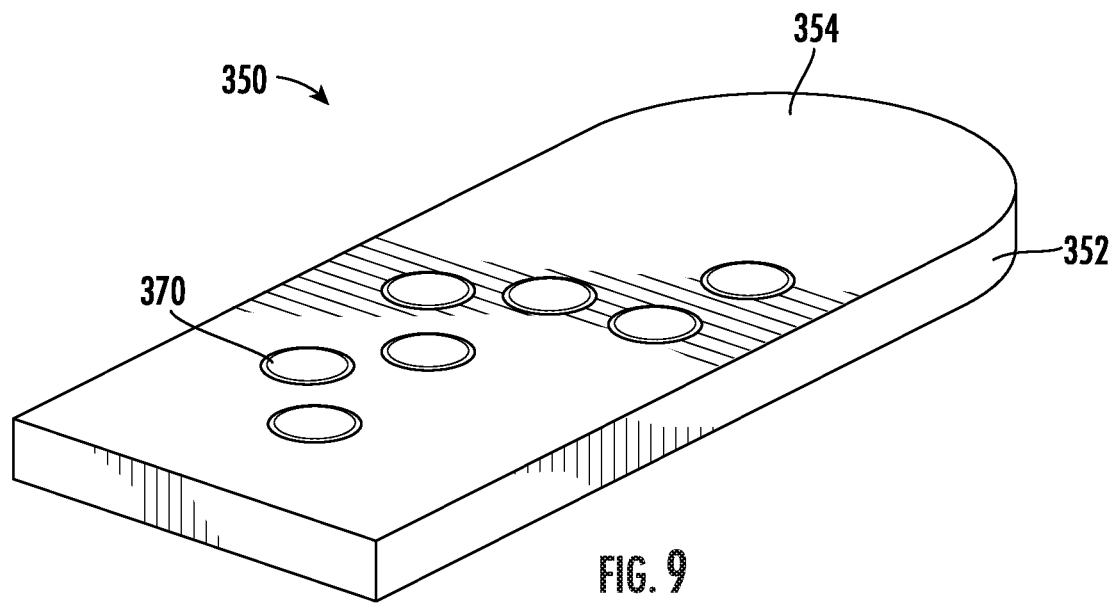
FIG. 9 illustrates a perspective view of another example of an embodiment of a cleaning cartridge that may be used in connection with the dialysis machine of FIG. 3.

In addition, and/or alternatively, referring to FIG. 9, the cleaning cartridge 350 may include a battery-operated vacuum. In one embodiment, the battery-operated vacuum may be positioned within the outer profile 352 of the cleaning cartridge. Alternatively, in one embodiment, the battery-operated vacuum may be coupled to the cleaning cartridge 350. Upon activation, the vacuum is arranged and configured to provide a sufficient amount of suction along the outer surface 354 to vacuum any foreign debris within the cassette port 300. For example, as illustrated, the cleaning cartridge 350 may include a plurality of vacuum ports 370. In use, with the cleaning cartridge 350 properly positioned within the cassette port 300, the vacuum ports 370 may be arranged and configured to align with the sensors, valves, actuators, pumps, etc. located within cassette port 300. Upon activation, the vacuum ports 370 are arranged and configured to provide a sufficient amount of suction, vacuum, etc. to remove any foreign debris away from the sensors, valves, actuators, pumps, etc. and out of the cassette port 300.

Figure 10:
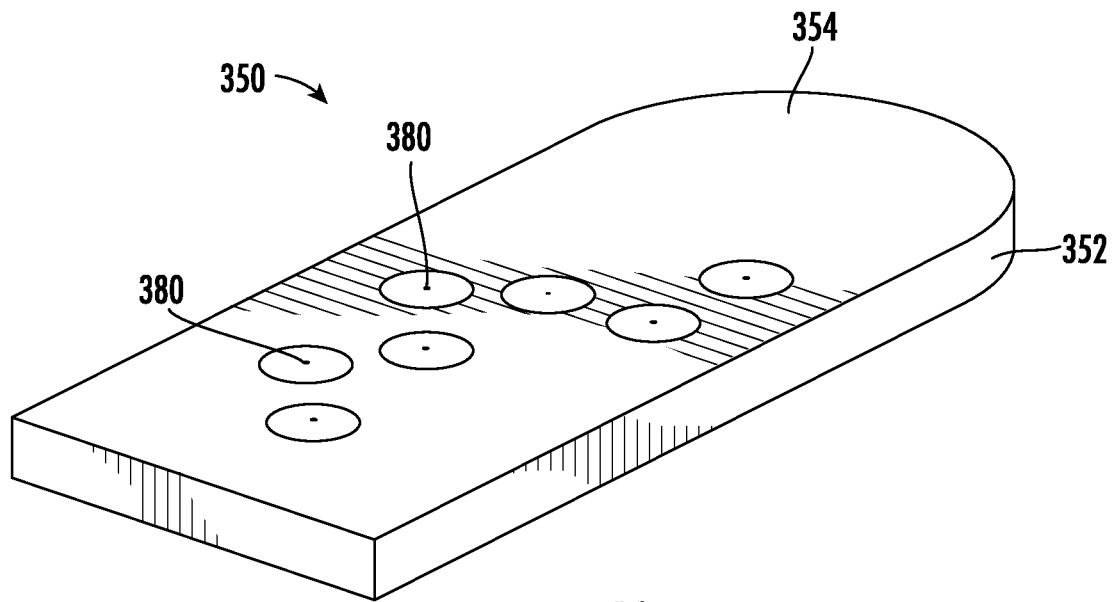
FIG. 10 illustrates a perspective view of another example of an embodiment of a cleaning cartridge that may be used in connection with the dialysis machine of FIG. 3.

Alternatively, referring to FIG. 10, the cleaning cartridge 350 may be arranged and configured with a battery-operated nozzle 380. In one embodiment, the battery-operated nozzle may be positioned within the outer profile 352 of the cleaning cartridge. Alternatively, in one embodiment, the battery-operated nozzle may be coupled to the cleaning cartridge 350. Upon activation, the nozzle 380 is arranged and configured to provide a sufficient amount of forced air to blow any foreign debris out of the cassette port 300. For example, as illustrated, the cleaning cartridge 350 may include a plurality of air nozzles 380. In use, with the cleaning cartridge 350 properly positioned within the cassette port 300, the air nozzles 380 may be arranged and configured to align with the sensors, valves, actuators, pumps, etc. located within cassette port 300. Upon activation, the air nozzles 380 are arranged and configured to provide a sufficient amount of forced air to remove any foreign debris away from the sensors, valves, actuators, pumps, etc. and out of the cassette port 300.

In either implementation, upon properly inserting the cleaning cartridge 350 within the cassette port 300, activation of the battery-operated vacuum or nozzle will collect or remove any foreign debris from the cassette port 300. In use, the battery may be rechargeable. Alternatively, the cleaning cartridge 350 may include disposable batteries.

Figure 11:
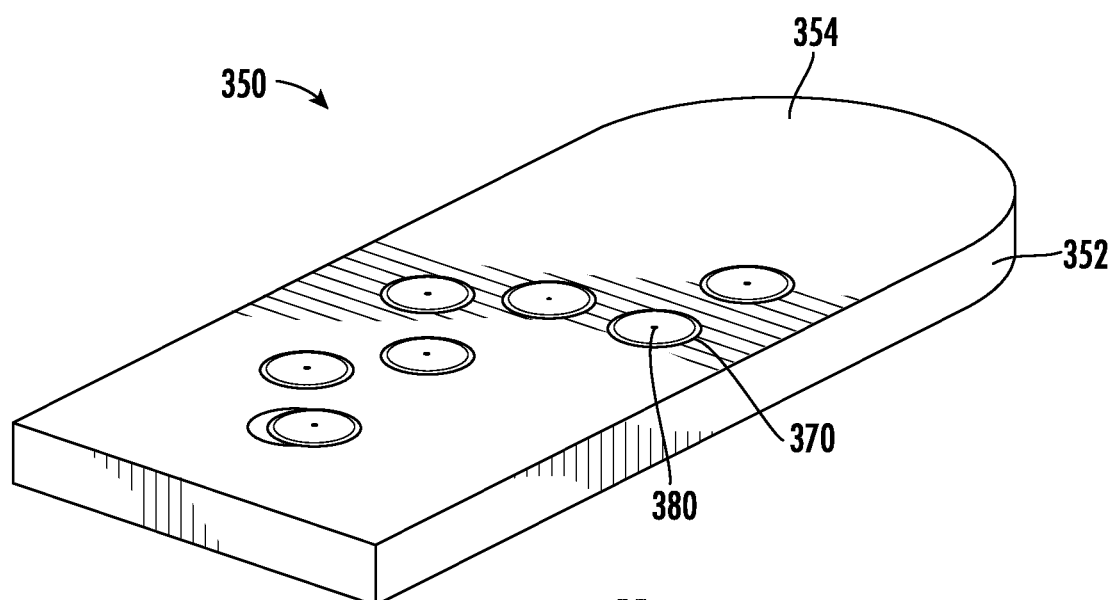
FIG. 11 illustrates a perspective view of another example of an embodiment of a cleaning cartridge that may be used in connection with the dialysis machine of FIG. 3.

Alternatively, referring to FIG. 11, the cleaning cartridge 350 may include a battery-operated vacuum and air nozzle system. Upon activation, the vacuum and air nozzle system is arranged and configured to provide a sufficient amount of forced air and suction to remove any foreign debris within the cassette port 300. For example, as illustrated, the cleaning cartridge 350 may include a plurality of vacuum ports 370 and air nozzles 380. In use, the air nozzles 380 may be positioned within the vacuum ports 370. Thereafter, with the cleaning cartridge 350 properly positioned within the cassette port 300, the air nozzles 380 may be aligned with the sensors, valves, actuators, pumps, etc. located within cassette port 300. The vacuum ports 370 may be arranged and configured to apply a ring around the air nozzles 380. Upon activation, the air nozzles 380 are arranged and configured to provide a sufficient amount of forced air to dislodge any foreign debris. At the same time, the vacuum is arranged and configured to provide a sufficient amount of suction to collect and remove the foreign debris. Thus arranged, upon properly inserting the cleaning cartridge 350 within the cassette port 300, activation of the battery-operated vacuum and nozzle system will remove and collect any foreign debris from the cassette port 300. In use, the battery may be rechargeable. Alternatively, the cleaning cartridge 350 may include disposable batteries.

In use, prior to commencing a PD treatment, a user can insert the cleaning cartridge 350 into the cassette port 300 formed in the PD machine 200 to perform a cleaning routine. In some embodiments, the PD machine 200 can be activated to cycle the actuators or pumps to loosen any foreign debris in the cassette port 300 to facilitate the transfer of the foreign debris to the cleaning cartridge 350. After completion of the cleaning routine, the user can remove the cleaning cartridge 350 and insert a cassette, e.g., cassette 320, into the cassette port 300 and begin the PD treatment.

Various aspects described herein have been explained in connection with the dialysis machine 200 having a particular configuration. It is contemplated that the various aspects described herein may be used with dialysis machines having other configurations, for example, different types of dialysis machines and/or dialysis machines having cassettes positionable in other configurations and having other features, such as different types of pumps and/or dialysate heating systems. The system described herein may be used with any appropriate dialysis machine and/or other medical devices utilizing disposable cassettes, including hemodialysis machines utilizing cassettes that handle medical fluids of a dialysis treatment, such as dialysate and/or blood.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method for cleaning a cassette port in a dialysis machine, the method comprising:
   inserting a cleaning cartridge into a cassette port of a dialysis machine, the dialysis machine for performing a dialysis treatment and including the cassette port arranged and configured to receive a disposable cassette in fluid communication with the patient; and
   removing the cleaning cartridge and any foreign debris from the cassette port, wherein the cleaning cartridge includes an outer surface arranged and configured to clean the cassette port so that upon removing the cleaning cartridge from the cassette port, any of the foreign debris located in the cassette port is removed from the cassette port.

2. The method of claim 1, wherein the cassette port is horizontally disposed in the dialysis machine.

3. The method of claim 1, wherein the outer surface includes a tacky film arranged and configured to collect any of the foreign debris.

4. The method of claim 1, wherein the outer surface includes coated fibers arranged and configured to collect foreign debris.

5. The method of claim 1, wherein the cleaning cartridge includes an electrostatic charge so that, upon inserting the cleaning cartridge within the cassette port, the cleaning cartridge attracts any of the foreign debris located in the cassette port.

6. The method of claim 1, wherein the cleaning cartridge includes a battery-operated vacuum so that, upon inserting the cleaning cartridge within the cassette port, activation of the vacuum collects any of the foreign debris located in the cassette port.

7. The method of claim 1, wherein the cleaning cartridge includes a battery-operated nozzle so that, upon inserting the cleaning cartridge within the cassette port, activation of the nozzle pushes any of the foreign debris located in the cassette port out of the dialysis machine.

8. The method of claim 1, wherein the cleaning cartridge includes a battery-operated vacuum and nozzle system so that, upon inserting the cleaning cartridge within the cassette port, activation of the vacuum and nozzle system pushes and collects any of the foreign debris located in the cassette port out of the dialysis machine.

\* \* \* \* \*